United States Patent
Shu et al.

(10) Patent No.: US 10,689,359 B2
(45) Date of Patent: Jun. 23, 2020

(54) CRYSTALS OF QUINAZOLINE DERIVATIVE AND PREPARATION METHOD THEREFOR

(71) Applicant: Xuanzhu Pharma Co., Ltd., Jinan, Shandong Province (CN)

(72) Inventors: Chutian Shu, Jinan (CN); Jinyuan Wang, Jinan (CN); Zhenhua Wang, Jinan (CN); Yuzhen Feng, Jinan (CN)

(73) Assignee: Xuanzhu Pharma Co., Ltd., Jinan, Shandong Province (CN)

(*) Notice: Subject to any disclaimer, the term of this patent is extended or adjusted under 35 U.S.C. 154(b) by 4 days.

(21) Appl. No.: 16/065,884

(22) PCT Filed: Dec. 23, 2016

(86) PCT No.: PCT/CN2016/111774
§ 371 (c)(1),
(2) Date: Jun. 25, 2018

(87) PCT Pub. No.: WO2017/107986
PCT Pub. Date: Jun. 29, 2017

(65) Prior Publication Data
US 2019/0002434 A1    Jan. 3, 2019

(30) Foreign Application Priority Data

Dec. 25, 2015 (CN) ............ 2015 1 0997569
Dec. 25, 2015 (CN) ............ 2015 1 0999065
Dec. 25, 2015 (CN) ............ 2015 1 0999109

(51) Int. Cl.
| C07D 401/12 | (2006.01) |
| A61K 31/517 | (2006.01) |
| A61K 31/519 | (2006.01) |
| A61P 11/00 | (2006.01) |
| A61P 17/00 | (2006.01) |
| A61P 13/08 | (2006.01) |
| A61P 35/00 | (2006.01) |

(52) U.S. Cl.
CPC .......... C07D 401/12 (2013.01); A61K 31/517 (2013.01); A61K 31/519 (2013.01); A61P 11/00 (2018.01); A61P 13/08 (2018.01); A61P 17/00 (2018.01); A61P 35/00 (2018.01); *C07B 2200/13* (2013.01)

(58) Field of Classification Search
CPC .................................................. C07D 401/12
See application file for complete search history.

(56) References Cited

U.S. PATENT DOCUMENTS

| 2007/0027170 A1 | 2/2007 | Soyka et al. |
| 2013/0184297 A1 | 7/2013 | Huang et al. |
| 2014/0161801 A1 | 6/2014 | Wu et al. |

FOREIGN PATENT DOCUMENTS

| CN | 102382065 A | 3/2012 |
| CN | 103965119 A | 8/2014 |

(Continued)

OTHER PUBLICATIONS

McMahon et al. (2000).*

(Continued)

*Primary Examiner* — Paul V Ward
(74) *Attorney, Agent, or Firm* — Christensen O'Connor Johnson Kindness PLLC

(57) ABSTRACT

The invention relates to Crystal form I, Crystal form II and Crystal form III of N-(4-((3-chloro-4-fluorophenyl)amino)-7-((7-methyl-7-azaspiro[3.5]nonan-2-yl)methoxy)quinazolin-6-yl)acrylamide represented by the following Formula (I), and preparation methods thereof, wherein the Crystal form I has an X-ray powder diffraction pattern having characteristic peaks at the 2θ positions of 6.7±0.2°, 7.9±0.2°, 8.6±0.2°, 12.0±0.2°, 13.9±0.2°, 15.9±0.2°, 17.3±0.2°, 18.3±0.2°, 18.7±0.2°, 21.0±0.2°, and 23.0±0.2°, as determined by using Cu-Kα radiation; the Crystal form II has an X-ray powder diffraction pattern having characteristic peaks at the 2θ positions of 6.9±0.2°, 8.5±0.2°, 14.8±0.2°, 15.6±0.2°, 16.7±0.2°, 17.1±0.2°, 17.9±0.2°, 18.7±0.2°, 19.1±0.2°, 21.5±0.2°, 23.5±0.2°, and 25.7±0.2°, as determined by using Cu-Kα radiation; and the Crystal form III has an X-ray powder diffraction pattern having characteristic peaks at the 2θ positions of 4.9±0.2°, 6.1±0.2°, 7.4±0.2°, 11.4±0.2°, 12.2±0.2°, 16.6±0.2°, and 18.4±0.2°, as determined by using Cu-Kα radiation.

Formula (I)

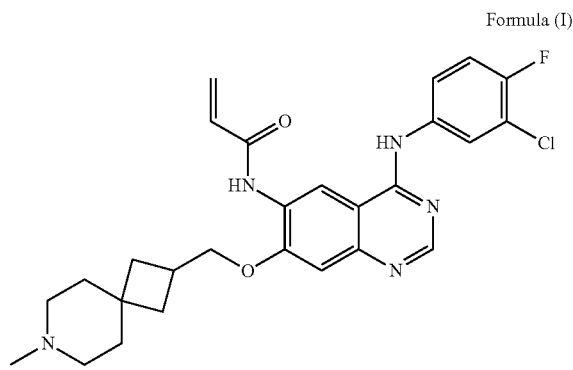

20 Claims, No Drawings

(56) References Cited

FOREIGN PATENT DOCUMENTS

| EP | 2612860 A1 | 7/2013 |
|---|---|---|
| EP | 3 395 810 A1 | 10/2018 |
| JP | 2010202668 A | 9/2010 |
| JP | 2013536253 A | 9/2013 |
| JP | 2014511336 A | 5/2014 |
| WO | 2012/027960 A1 | 3/2012 |
| WO | 2012121764 A1 | 9/2012 |
| WO | 2012/159457 A1 | 11/2012 |

OTHER PUBLICATIONS

Pinedo et al. (2000).*
Neidle et al., (2008) Cancer Drug Design and Discovery (Elsevier/Academic Press). pp. 427-431.*
International Search Report dated Mar. 8, 2017, issued in International Application No. PCT/CN2016/111774, filed Dec. 23, 2016, 8 pages.
Extended European Search Report dated May 23, 2019, issued in corresponding European Application No. EP 16877796.9, filed Dec. 23, 2016, 7 pages.
Ashizawa, K., "Optimization of salt/crystal Forms and Crystallization Technology," Pharm Tech Japan (18)10: 81-96, 2002.
Notice of Reasons for Rejection dated Aug. 20, 2019, issued in corresponding Japanese Application No. 2018-533083, filed Oct. 27, 2016, 6 pages.

* cited by examiner

CRYSTALS OF QUINAZOLINE DERIVATIVE AND PREPARATION METHOD THEREFOR

TECHNICAL FIELD

The present invention relates to crystals of quinazoline derivative N-(4-((3-chloro-4-fluorophenyl)amino)-7-((7-methyl-7-azaspiro[3.5]nonan-2-yl)methoxy)quinazolin-6-yl)acrylamide, preparation methods and uses thereof.

BACKGROUND ART

Protein tyrosine kinases (PTKs) are a class of enzymes that can catalytically transfer a phosphate group from ATP to the tyrosine residue of a protein substrate, and play a role in normal cell growth. Many growth factor receptor proteins work via tyrosine kinases, and affect signal transduction pathways through this process, thereby modulating cell growth. However, under some conditions, these receptors become abnormal due to either mutation or over-expression, cause uncontrolled cell proliferation, lead to tumor growth, and finally result in a well-known disease—cancer. Growth factor receptor protein tyrosine kinase inhibitors play a role in treatment of cancer and other diseases characterized by uncontrolled or abnormal cell growth, by inhibiting said phosphorylation process.

Epidermal growth factor receptor (EGFR) is a multifunctional glycoprotein that is widely distributed on the cell membranes of various tissues in human body, and is an avian erythroblastic leukemia viral (v-erb-b) oncogene homolog. Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). Clinical studies show that EGFR and the like are over-expressed in many tumors, for example, epithelial-derived tumors such as squamous cell carcinoma of head and neck, breast cancer, rectal cancer, ovarian cancer, prostate cancer, and non-small cell lung cancer. By competing with ATP for binding kinase catalytic sites in the intracellular region, Pan-HER tyrosine kinase inhibitors block the autophosphorylation of tyrosine in the molecule, block the activation of tyrosine kinase, and inhibit the activation of HER family, thereby inhibiting cell cycle progression, accelerating cell apoptosis, and exerting a therapeutic action.

After binding to ligand, EGFR forms a dimer with a subgroup of HER family, and then binds to ATP to activate the tyrosine kinase activity of EGFR itself, resulting in the autophosphorylation at several tyrosine sites of the intracellular kinase region. Pan-HER tyrosine kinase inhibitors have good effect of inhibiting tumor growth, by acting on EGFR and HER2/4 simultaneously and inhibiting the activation of HER family.

The quinazoline derivative of the following Formula (I), N-(4-((3-chloro-4-fluorophenyl)amino)-7-((7-methyl-7-azaspiro[3.5]nonan-2-yl)methoxy)quinazolin-6-yl)acrylamide (which was disclosed in the patent application WO2012027960A1), is an irreversible Pan-HER tyrosine kinase inhibitor, can effectively inhibit EGFR, and also has an inhibitory effect on HER2/4. The drug having an irreversible inhibitory effect on HER/ErbB family can not only enhance the activity of drugs, but also can reduce the generation of drug resistance, and has a significantly inhibitory effect on erlotinib-resistant H1975 cell line.

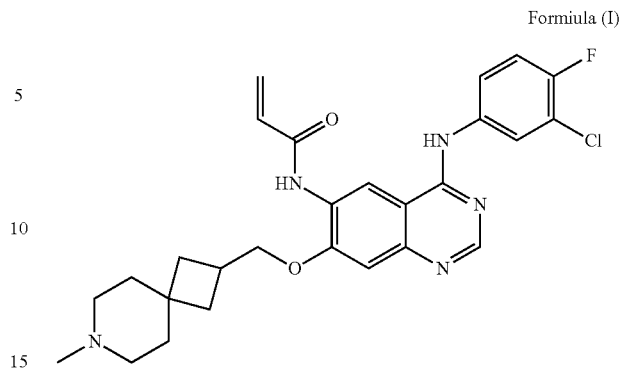

Formiula (I)

Development of crystals is very important in drug development. Different forms of a compound have different bioavailability and solubility. Crystal forms have a great influence on the stability, processing property, bioavailability, solubility, formulation, and industrial production and transportation of compounds.

CONTENTS OF INVENTION

The purpose of the invention is to provide crystals of N-(4-((3-chloro-4-fluorophenyl)amino)-7-((7-methyl-7-azaspiro[3.5]nonan-2-yl)methoxy)quinazolin-6-yl)acrylamide represented by the Formula (I), preparation methods and uses thereof.

In order to achieve the purpose, the inventors conducted deep researches, and surprisingly found that a class of crystals of N-(4-((3-chloro-4-fluorophenyl)amino)-7-((7-methyl-7-azaspiro[3.5]nonan-2-yl)methoxy)quinazolin-6-yl)acrylamide represented by the Formula (I) had excellent stability and pharmacokinetic properties, and therefore accomplished the invention.

In particular, the invention relates to the following technical solutions.

(1) Crystal form I of N-(4-((3-chloro-4-fluorophenyl)amino)-7-((7-methyl-7-azaspiro[3.5]nonan-2-yl)methoxy)quinazolin-6-yl)acrylamide represented by Formula (I), has the following crystal structure: an X-ray powder diffraction pattern having characteristic peaks at the 2θ positions of 6.7±0.2°, 7.9±0.2°, 8.6±0.2°, 12.0±0.2°, 13.9±0.2°, 15.9±0.2°, 17.3±0.2°, 18.3±0.2°, 18.7±0.2°, 21.0±0.2°, and 23.0±0.2°, as determined by using Cu-Kα radiation,

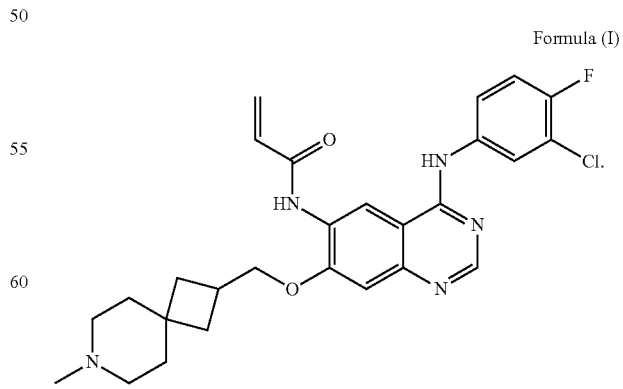

Formula (I)

(2) The Crystal form I according to Item (1), has the following crystal structure: the X-ray powder diffraction pattern further having characteristic peaks at the 2θ positions of 16.2±0.2°, 23.0±0.2°, 23.4±0.2°, 25.3±0.2°, 26.0±0.2°, 26.5±0.2°, 27.7±0.2°, and 28.0±0.2°, and further having characteristic peaks at the 2θ positions of 13.6±0.2°, 21.5±0.2°, 21.9±0.2°, and 32.2±0.2°, as determined by using Cu-Kα radiation.

(3) The Crystal form I according to Item (1), has a DSC thermogram having an endothermic conversion peak at 75-150° C., and a maximum endothermic conversion temperature of 113-114° C., preferably a maximum endothermic conversion temperature of 113.85° C.

(4) The Crystal form I according to Item (1), is preferably a hydrate having a water content of 2.5%-4%, preferably 2.5%-3.0%.

(5) The Crystal form I according to Item (1), is preferably a monohydrate.

The invention further provides a method for preparing Crystal form I of a compound of Formula (I), wherein the compound of Formula (I) can be synthesized by the method as disclosed in the international patent application WO2012027960A1. Crystal form I of a compound of Formula (I) (hereafter referred to as Crystal form I) can be prepared by the following method:

(6) A method for preparing the Crystal form I according to any one of Items (1)-(5), comprising the following steps: a compound of Formula (I) is dissolved in a lower nitrile organic solvent or in a mixed solvent of a lower ester organic solvent and a lower alcohol organic solvent, and then subjected to addition of a poor solvent or recrystallization to produce a crystal, and then the crystal is subjected to filtration and drying to obtain Crystal form I.

The lower nitrile organic solvent is preferably acetonitrile; the lower ester organic solvent is preferably ethyl acetate or ethyl formate; the lower alcohol organic solvent is preferably methanol, ethanol or isopropanol; the poor solvent is preferably water, or a lower polar solvent such as alkane or ether.

The mixed solvent consisting of a lower ester organic solvent and a lower alcohol organic solvent is further preferably ethyl acetate/isopropanol (10:1).

(7) Crystal form II of N-(4-((3-chloro-4-fluorophenyl)amino)-7-((7-methyl-7-azaspiro[3.5]nonan-2-yl)methoxy)quinazolin-6-yl)acrylamide represented by Formula (I), has the following crystal structure: an X-ray powder diffraction pattern having characteristic peaks at the 2θ positions of 6.9±0.2°, 8.5±0.2°, 14.8±0.2°, 15.6±0.2°, 16.7±0.2°, 17.1±0.2°, 17.9±0.2°, 18.7±0.2°, 19.1±0.2°, 21.5±0.2°, 23.5±0.2°, and 25.7±0.2°, as determined by using Cu-Kα radiation.

(8) The Crystal form II according to Item (7), has the following crystal structure: the X-ray powder diffraction pattern further having characteristic peaks at the 2θ positions of 11.6±0.2°, 17.3±0.2°, 22.1±0.2°, 26.1±0.2°, and 28.3±0.2°, and further having characteristic peaks at the 2θ positions of 14.0±0.2°, 16.0±0.2°, 19.7±0.2°, 20.6±0.2°, 22.4±0.2°, 24.5±0.2°, 28.6±0.2°, 31.7±0.2°, and 34.6±0.2°, as determined by using Cu-Kα radiation.

(9) The Crystal form II according to Item (7), has a DSC thermogram having an endothermic conversion peak at 75-169° C., and a maximum endothermic conversion temperature of 123-124° C., preferably a maximum endothermic conversion temperature of 123.54° C.

(10) The Crystal form II according to Item (7), which is preferably a hydrate having a water content of 3%-4%, preferably 3.3% or 3.4%.

(11) The Crystal form II according to Item (7), which is preferably a monohydrate.

The invention further provides a method for preparing Crystal form II of a compound of Formula (I), wherein the compound of Formula (I) can be synthesized by the method as disclosed in the international patent application WO2012027960A1. Crystal form II of a compound of Formula (I) (hereafter referred to as Crystal form II) can be prepared by the following method.

(12) A method for preparing the Crystal form II according to any one of Items (7)-(11), comprising the following steps: a compound of Formula (I) is dissolved in a lower ester organic solvent, an aromatic hydrocarbon organic solvent, or a mixed solvent of a lower ester organic solvent and a lower alcohol organic solvent, and then subjected to addition of a poor solvent or recrystallization to produce a crystal, and then the crystal is subjected to filtration and drying to obtain Crystal form II; preferably, Crystal form II is obtained by means of recrystallization with a lower ester organic solvent.

The lower ester organic solvent is selected from the group consisting of ethyl acetate, ethyl formate, methyl acetate and isopropyl acetate; the aromatic hydrocarbon organic solvent is toluene; the lower alcohol organic solvent is selected from the group consisting of methanol, ethanol and isopropanol; the poor solvent is preferably water, or a lower polar solvent such as alkane or ether.

The mixed solvent of a lower ester organic solvent and a lower alcohol organic solvent is preferably ethyl acetate/methanol, isopropyl acetate/isopropanol, or ethyl acetate/isopropanol (15:1).

(13) Crystal form III of N-(4-((3-chloro-4-fluorophenyl)amino)-7-((7-methyl-7-azaspiro[3.5]nonan-2-yl)methoxy)quinazolin-6-yl)acrylamide represented by Formula (I), has the following crystal structure: an X-ray powder diffraction pattern having characteristic peaks at the 2θ positions of 4.9±0.2°, 6.1±0.2°, 7.4±0.2°, 11.4±0.2°, 12.2±0.2°, 16.6±0.2°, and 18.4±0.2°, as determined by using Cu-Kα radiation.

(14) The Crystal form III according to Item (13), has the following crystal structure: the X-ray powder diffraction pattern further having characteristic peaks at the 2θ positions of 11.2±0.2°, 13.4±0.2°, 14.8±0.2°, 19.2±0.2°, 20.4±0.2°, 20.8±0.2°, 23.2±0.2°, 23.8±0.2°, 25.7±0.2°, and 27.5±0.2°, and further having characteristic peaks at the 2θ positions of 9.2±0.2°, 22.4±0.2°, and 30.1±0.2°, as determined by using Cu-Kα radiation.

(15) The Crystal form III according to Item (13), has a DSC thermogram having an endothermic conversion peak at 50-125° C., and a maximum endothermic conversion temperature of 96-97° C., preferably a maximum endothermic conversion temperature of 96.79° C.

(16) The Crystal form III according to Item (13), is a hydrate having a water content of 2.5%-4%, preferably 2.5-3.5%, more preferably 2.5-3.0%, most preferably 2.69%.

(17) The Crystal form III according to Item (13), is a monohydrate.

In addition, the invention further provides a method for preparing Crystal form III of a compound of Formula (I). The compound of Formula (I) can be synthesized by the method as disclosed in the international patent application WO2012027960A1. Crystal form III of a compound of Formula (I) (hereafter referred to as Crystal form III) can be prepared by the following method.

(18) A method for preparing the Crystal form III according to any one of Items (13)-(17), comprising the following steps: a compound of Formula (I) is subjected to recrystallization using a lower alcohol organic solvent or a lower halo hydrocarbon organic solvent to produce a solid, and then the solid is subjected to filtration and drying to obtain Crystal form III.

The lower alcohol organic solvent is preferably methanol, ethanol, propanol or isopropanol; the lower halo hydrocarbon organic solvent is preferably dichloromethane or chloroform.

(19) A method for preparing the Crystal form III according to any one of Items (13)-(17), comprising the following steps: a compound of Formula (I) is dissolved in a lower ketone organic solvent, and then subjected to addition of an alicyclic hydrocarbon organic solvent dropwise to produce a solid, and then the solid is subjected to filtration and drying to obtain Crystal form III.

The lower ketone organic solvent is preferably acetone, butanone, methyl butanone or methyl isobutyl ketone; the alicyclic hydrocarbon organic solvent is preferably cyclopentane or cyclohexane.

Beneficial Effects of Invention

Crystal form I, Crystal form II and Crystal form III of a compound of Formula (I) as prepared in the invention have good solubility in water, a buffer or an organic solvent, and have good stability for grinding and tableting, which is favorable for use in manufacture of a medicament.

Crystal form I, Crystal form II and Crystal form III of a compound of Formula (I) as prepared in the invention have better pharmacokinetics, longer half-life, and higher drug exposure in vivo than its amorphous form.

Crystal form I, Crystal form II and Crystal form III of a compound of Formula (I) as prepared in the invention have good stability, can be prepared by simple processes, have stable quality, have good physicochemical property, and can be produced industrially on a large scale.

DESCRIPTION OF THE DRAWINGS

FIG. 1 shows the X-ray powder diffraction (XRPD) pattern of Crystal form I of a compound of Formula (I), wherein the ordinate represents diffraction intensity (CPS), and the abscissa represents the diffraction angle (2θ).

FIG. 2 shows the TGA thermogram of Crystal form I of a compound of Formula (I), wherein the ordinate represents mass percent (%), and the abscissa represents a complex coordinate time-temperature (° C.).

FIG. 3 shows the DSC thermogram of Crystal form I of a compound of Formula (I), wherein the ordinate represents heat flow (W/g), and the abscissa represents temperature (° C.).

FIG. 4 shows the X-ray powder diffraction (XRPD) pattern of Crystal form II of a compound of Formula (I), wherein the ordinate represents diffraction intensity (CPS), and the abscissa represents the diffraction angle (2θ).

FIG. 5 shows the DSC thermogram of Crystal form II of a compound of Formula (I), wherein the ordinate represents heat flow (W/g), and the abscissa represents temperature (° C.).

FIG. 6 shows the TGA thermogram of Crystal form II of a compound of Formula (I), wherein the ordinate represents mass percent (%), and the abscissa represents a complex coordinate time-temperature (° C.).

FIG. 7 shows the X-ray powder diffraction (XRPD) pattern of Crystal form III of a compound of Formula (I), wherein the ordinate represents diffraction intensity (CPS), and the abscissa represents the diffraction angle (2θ).

FIG. 8 shows the TGA thermogram of Crystal form III of a compound of Formula (I), wherein the ordinate represents mass percent (%), and the abscissa represents a complex coordinate time (min)-temperature (° C.).

FIG. 9 shows the DSC thermogram of Crystal form III of a compound of Formula (I), wherein the ordinate represents heat flow (W/g), and the abscissa represents temperature (° C.).

SPECIFIC MODES FOR CARRYING OUT THE INVENTION

In the description and claims of the present application, a compound is denominated based on its chemical structural formula. If the name of a compound used herein is not consistent with the chemical structural formula, the chemical structural formula or chemical reaction formula will prevail.

In the present application, unless otherwise specified, the scientific and technical terms used herein have the meanings as generally understood by a person skilled in the art. However, in order to understand the invention better, definitions and explanations are provided for a part of relevant terms. In addition, if the definitions and explanations of the terms provided in the present application are different from the meanings generally understood by a person skilled in the art, the definitions and explanations of the terms provided in the present application shall prevail.

In the expressions "a lower nitrile organic solvent", "a lower ester organic solvent", "a lower halo hydrocarbon organic solvent" and "a lower alcohol organic solvent" as used in the invention, the term "lower" means that an organic solvent has 1-6 carbon atoms in the molecule, preferably, an organic solvent has 1-4 carbon atoms.

The term "a poor solvent" as used in the invention refers to a solvent, in which a compound of Formula (I) has a low solubility, selected from the group consisting of water, and a low polar solvent such as alkane or ether.

The term "organic solvent" as used in the invention may refer to any commercially available organic solvent, or a mixed solvent. The mixed solvent refers to a mixed solvent consisting of two or more organic solvents at a certain ratio by volume, or a mixed solvent consisting of an organic solvent and water at a certain ratio by volume, preferably, a mixed solvent of water and a lower alcohol organic solvent, a lower cyclic ether organic solvent, a lower ketone organic solvent or a lower nitrile organic solvent at any ratio, including, but not limited to the following mixed solvent systems and ratios: methanol/water (10:1), ethanol/water (10:1), acetonitrile/water (10:1), tetrahydrofuran/water (10:1), acetone/water (10:1, 3:1-4:1), 1,4-dioxane/water (10:1), etc.; methanol/acetonitrile, methanol/tetrahydrofuran, methanol/dichloromethane, methanol/ethyl acetate, methanol/methyl tert-butyl ether, methanol/n-hexane, methanol/toluene, ethanol/acetonitrile, ethanol/tetrahydrofuran, ethanol/dichloromethane, ethanol/ethyl acetate, ethanol/methyl tert-butyl ether, ethanol/n-hexane, ethanol/toluene, isopropanol/acetonitrile, isopropanol/tetrahydrofuran, isopropanol/dichloromethane, ethyl acetate/isopropanol, isopropanol/methyl tert-butyl ether, isopropanol/n-hexane, isopropanol/toluene, acetonitrile/methyl tert-butyl ether, acetonitrile/ethyl acetate, acetonitrile/dichloromethane, acetonitrile/tetrahydrofuran, acetonitrile/n-hexane, acetonitrile/toluene, methyl tert-butyl ether/ethyl acetate, methyl tert-butyl ether/dichloromethane, methyl tert-butyl ether/tetrahydrofuran, methyl tert-butyl ether/n-hexane, methyl tert-butyl ether/toluene, ethyl acetate/dichloromethane, ethyl acetate/tetrahydrofuran, ethyl acetate/n-hexane, ethyl acetate/toluene, dichloromethane/tetrahydrofuran, dichloromethane/n-hexane, dichloromethane/toluene, tetrahydrofuran/n-hexane, tetrahydrofuran/toluene, n-hexane/toluene (the mixed solvents above preferably have a ratio of 1:1 by volume), ethyl acetate/isopropanol (10:1, 15:1), etc.; preferably a mixed solvent consisting of an organic solvent having 1-4 carbon atoms or water and an organic solvent having 1-4 carbon atoms.

The term "2θ angle" as used in the invention means that X-ray diffraction analysis is based on Bragg's law (Bragg's law is 2d sin θ=nλ), wherein "θ" is the glancing angle or Bragg angle, i.e., the complementary angle for the angle of incidence, and "2θ" is the diffraction angle; "d" is the interplanar spacing between adjacent lattice planes in the crystal lattice, expressed as Å; "λ" is the wavelength of X-ray; and "n" is any positive integer, i.e., the "order" of diffraction. In the XRPD pattern, the abscissa of powder diffraction peaks is the 2θ angle, and the 2θ position of peak has a deviation of ±0.3°, preferably of ±0.2°. When the crystal form of the invention is determined by X-ray diffraction, sometimes there is a deviation in the measured peaks due to the measurement instrument or conditions. Therefore, when determining a crystal structure, the deviation shall be taken into account. Thus, when determining the degree of 2θ, a deviation of ±0.2 is employed by the applicant.

Differential scanning calorimetry (DSC) is a thermoanalytical technique. Within a programmed temperature range, the difference in power input (such as the amount of heat) required for a sample and reference is measured as a function of temperature. The curve recorded by differential scanning calorimeter is also called DSC curve, which uses heat absorption or heat release rate (heat flow dH/dt (unit: mJ/s)) as the ordinate, and uses temperature T or time t as the abscissa, and can be used to determine a lot of thermodynamic and kinetic parameters, for example, specific heat capacity, reaction heat, transition heat, phase diagram, reaction rate, crystallization rate, polymer crystallinity, sample purity, and so on. The method can be applied within a wide temperature range (−175~725° C.), and has a high resolution, and a small amount of sample is required.

Thermogravimetric Analysis (TGA) is a thermoanalytical technique that measures the mass of a test sample as the temperature changes within a programmed temperature range. It is used to study the thermal stability and composition of a substance. TGA measures the mass of a sample as the temperature (or time) changes within a programmed temperature range. When a test substance sublimes, vaporizes, decomposes or loses water of crystallization during heating, the mass of the test substance will change. In this case, the thermogravimetric curve is not a straight line, and drops to some extent. By analyzing the thermogravimetric curve, the temperature, at which the test substance changes, can be determined; and based on the lost weight, the lost substance such as water of crystallization can be determined by calculation. By conducting TGA experiments, it is helpful to study the change in nature of crystals, for example, physical phenomena of substances such as melting, evaporation, sublimation and adsorption; and is also helpful to study the chemical phenomena of substances, such as dissociation, oxidation, reduction, thermal stability, decomposition process, quantitative analysis of ingredients, effects of additives and fillers, moisture and volatiles, and reaction kinetics. Thermogravimetric analysis can be generally classified into two types: dynamic TGA (temperature increasing) and static TGA (isothermal). The curve obtained by thermogravimetric test is called the thermogravimetric curve (TG curve). TG curve uses mass as the ordinate (the mass reduces from top to bottom), and temperature (or time) as the abscissa (the temperature (or time) increases from left to right).

X-ray Powder Diffraction (XRPD) means that when a beam of X-rays reaches an object, it is scattered by the atoms in the object, each atom produces scattered waves, and these waves interfere with each other, resulting in diffraction. As a result of the superposition of scattered waves, the X-rays have the intensity enhanced in some directions, and weakened in other directions. The crystal structure can be obtained by analysis of diffraction results. X-ray diffractometer can accurately determine the crystal structure, texture and stress of a substance, and accurately achieve phase analysis, qualitative analysis, and quantitative analysis by utilizing diffraction theory. For crystal material, when the crystal to be measured is at different angles relative to the incident beam, those crystal faces satisfying the Bragg diffraction can be detected, which are presented by the diffraction peaks with different diffraction intensity in the XRD pattern. Non-crystal materials only have short-range ordered arrangement of several atoms in their structures, instead of long-range ordered arrangement of atoms in crystal structure. Therefore, non-crystal materials only have some diffuse scattering peaks in XRD pattern.

The invention further provides use of Crystal form I, Crystal form II or Crystal form III of a compound of Formula (I) in manufacture of a medicament for treating hyperproliferative disease and chronic obstructive pulmonary disease.

The hyperproliferative disease according to the invention is selected from the group consisting of cancer and noncancerous disease; the cancer is selected from the group consisting of brain tumor, lung cancer, squamous epithelial cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, esophageal adenocarcinoma, esophageal squamous cell carcinoma, non-Hodgkin's lymphoma, central nervous system tumor, prostate cancer and thyroid cancer; the noncancerous disease is benign hyperplasia of skin or prostate.

The invention further provides a pharmaceutical formulation comprising the Crystal form I, Crystal form II or Crystal form III of a compound of Formula (I) and one or more pharmaceutically acceptable carriers and/or diluents, which may be any pharmaceutically acceptable dosage form, such as an oral formulation and an injection. When being prepared into an oral formulation, a suitable filler, a suitable binding agent, a suitable disintegrating agent or a suitable lubricant, etc. may be added.

The invention is further described, but is not restricted by the following embodiments. A person skilled in the art, based on the teachings of the invention, can make various modifications or improvements without departing from the basic spirit and scope of the invention.

Experimental Solutions

The exemplified experimental solutions are provided for a part of the compounds according to the invention in order to show the favorable activity and beneficial technical effects of the compounds according to the invention. However, it should be understood that the following experimental solutions are provided only for the purpose of illustrating the invention, rather than restricting the scope of the invention. A person skilled in the art, based on the teachings contained in the description, can make suitable modifications or alterations to the technical solutions of the invention without departing from the spirit and scope of the invention.

Experimental Example 1. Study on Stability of Crystal Form I, Crystal Form II and Crystal Form III Conditions for studying Crystal form I (influencing factor): Crystal form I was kept separately under conditions of 60° C.-uncovered, 60° C.-covered, 40° C.-RH 75%-uncovered, 40° C.-RH 75%-covered, RH 92.5%-uncovered, RH 75%-uncovered, light (UV)-uncovered, light (Vis)-uncovered experimental conditions for 10 days, and samples were taken at Day 5 and Day 10, and compared with the sample at Day 0. The samples were tested for character, relevant substances, moisture content, XRPD pattern, etc.

Conditions for studying Crystal form II: Crystal form II was kept separately under conditions of high temperature (60° C. uncovered and covered), high moisture (25° C., RH 75%) and (25° C., RH 92.5%) uncovered, 40° C.-RH75% uncovered, 40° C.-RH75% covered, and light; and samples were taken at Day 5 and Day 10, and compared with the sample at Day 0. The samples were tested for relevant substances, content, character, moisture content, XRPD pattern, etc. During the study, the uncovered experimental samples were kept in cultured dishes in the air.

Conditions for studying Crystal form III: ① Crystal form III was kept separately under conditions of high temperature (60° C.) uncovered and covered, high moisture (25° C., RH 75% and 25° C., RH 92.5%) uncovered, and samples were taken at Day 5 and Day 10; ② Crystal form III was kept separately under conditions of 40° C., RH75% uncovered and covered, and samples were taken at Day 5 and Day 10; ③ Crystal form III was kept uncovered under the condition of light for 5 days, and kept uncovered under UV light for 10 days, and samples were taken; the samples were compared with the samples at Day 0, and were tested for relevant substances, character, moisture content, crystal characteristics, etc. During the study, the uncovered experimental samples were kept in cultured dishes in the air.

Test sample: Crystal form I, Crystal form II and Crystal form III of a compound of Formula (I), the preparation methods of which could be found in the following Examples.

Experimental Conditions:

With respect to relevant substances, in accordance with High Performance Liquid Chromatography in Appendix V D in Pharmacopoeia of the People's Republic of China (2010), the samples were determined by area normalization method.

Operation Conditions

Instrument: High Performance Liquid Chromatographic Instrument (Agilent 1200/1260 series)

Chromatographic column: chromatographic column using octylsilane chemically bonded silica as filler (HC-$C_8$, 4.6×250 mm, 5 μm)

Column temperature: 30° C.

Detection wavelength: 230 nm

Mobile phase: mobile phase consisting of 0.03 mol/L diammonium hydrogen phosphate/0.03 mol/L sodium perchlorate solution-acetonitrile, and reversed-phase gradient elution was employed.

Flow rate: 1.0 mL/min

Injection volume: 10 μL

Method for determining moisture content: the moisture content was determined in accordance with First Method for Determining Moisture Content B (Coulometric Titration) in Appendix VIII M in Pharmacopoeia of the People's Republic of China (2010).

Experimental Result

TABLE 1

Result of stability of Crystal form I

|  | Conditions | Character | Moisture content (%) | Relevant substance (%) | Crystal form |
|---|---|---|---|---|---|
|  | 0 day | light yellow powder | 5.0 | 0.78 | crystallinity |
| 5 days | 60° C. uncovered | light yellow powder | 4.9 | 1.3 | the same as Day 0 |
|  | 60° C. covered | light yellow powder | 5.0 | 0.75 | the same as Day 0 |
|  | 40° C./RH75% uncovered | light yellow powder | 5.4 | 0.76 | the same as Day 0 |
|  | 40° C./RH75% covered | light yellow powder | 5.1 | 0.74 | the same as Day 0 |
|  | visible light | light yellow powder | 5.1 | 0.74 | the same as Day 0 |
|  | RH-92.5% | light yellow powder | 5.5 | 0.78 | the same as Day 0 |
|  | RH-75% | light yellow powder | 5.5 | 0.78 | the same as Day 0 |
| 10 days | 60° C. uncovered | light yellow powder | 4.6 | 1.4 | the same as Day 0 |
|  | 60° C. covered | light yellow powder | 4.8 | 0.78 | the same as Day 0 |
|  | 40° C./RH75% uncovered | light yellow powder | 5.2 | 0.79 | the same as Day 0 |
|  | 40° C./RH75% covered | light yellow powder | 4.9 | 0.73 | the same as Day 0 |
|  | RH-92.5% | light yellow powder | 5.8 | 0.79 | the same as Day 0 |
|  | RH-75% | light yellow powder | 5.7 | 0.70 | the same as Day 0 |
|  | UV light | light yellow powder | 5.2 | 0.89 | the same as Day 0 |

As seen from the data in Table 1, the result of studying Crystal form I of a compound of Formula (I) under influencing factor condition for 10 days showed that under the conditions of high moisture RH-75%, RH-92.5%, moisture content increased by 0.7% and 0.8%, respectively; and under the conditions of 60° C.-uncovered, UV light, the impurities increased to some extent, respectively, there was almost no change in the other items studied, and the crystal form was also kept well, i.e., the samples were relatively stable.

TABLE 2

Result of stability of Crystal form II

|  | Conditions | Character | Moisture content (%) | Relevant substance (%) | Crystal form |
|---|---|---|---|---|---|
|  | 0 day | light yellow powder | 3.5 | 0.37 | Crystal form II |
| 5 days | 60° C. uncovered | light yellow powder | 3.6 | 0.35 | the same as Day 0 |
|  | 60° C. covered | light yellow powder | 3.6 | 0.33 | the same as Day 0 |
|  | 40° C.-RH75% uncovered | light yellow powder | 3.7 | 0.38 | the same as Day 0 |
|  | 40° C.- | light yellow | 3.6 | 0.34 | the same |

TABLE 2-continued

Result of stability of Crystal form II

| | Conditions | Character | Moisture content (%) | Relevant substance (%) | Crystal form |
|---|---|---|---|---|---|
| | RH75% covered light | powder | | | as Day 0 |
| | light | light yellow powder | 3.7 | 0.35 | the same as Day 0 |
| | RH-92.5% | light yellow powder | 3.7 | 0.36 | the same as Day 0 |
| | RH-75% | light yellow powder | 3.6 | 0.35 | the same as Day 0 |
| 10 days | 60° C. uncovered | light yellow powder | 3.7 | 0.43 | the same as Day 0 |
| | 60° C. covered | light yellow powder | 3.7 | 0.36 | the same as Day 0 |
| | 40° C.-RH75% uncovered | light yellow powder | 3.8 | 0.33 | the same as Day 0 |
| | 40° C.-RH75% covered | light yellow powder | 3.6 | 0.33 | the same as Day 0 |
| | light | light yellow powder | 3.7 | 0.35 | the same as Day 0 |
| | RH-92.5% | light yellow powder | 3.7 | 0.34 | the same as Day 0 |
| | RH-75% | light yellow powder | 3.7 | 0.36 | the same as Day 0 |

As seen from the data in Table 2, the result of studying Crystal form II of a compound of Formula (I) under influencing factor condition for 10 days showed that there was no significant change in impurities; the XRPD pattern test showed that there was no change in Crystal form, and there was almost no change in other items studies, i.e., the samples were relatively stable.

TABLE 3

Result of stability of Crystal form III

| | Conditions | Character | Moisture content (%) | Total relevant substances (%) |
|---|---|---|---|---|
| | 0 day | light yellow powder | 3.5 | 0.66 |
| 5 days | 60° C. uncovered | light yellow powder | 3.5 | 0.94 |
| | 60° C. covered | light yellow powder | 3.6 | 0.60 |
| | 40° C./RH75% uncovered | light yellow powder | 3.9 | 0.63 |
| | 40° C./RH75% covered | light yellow powder | 3.6 | 0.57 |
| | Visible light | light yellow powder | 3.7 | 0.68 |
| | RH-92.5% | light yellow powder | 4.0 | 0.58 |
| | RH-75% | light yellow powder | 4.0 | 0.62 |
| 10 days | 60° C. uncovered | light yellow powder | 3.4 | 1.1 |
| | 60° C. covered | light yellow powder | 3.5 | 0.64 |
| | 40° C./RH75% uncovered | light yellow powder | 3.9 | 0.62 |
| | 40° C./RH75% covered | light yellow powder | 3.6 | 0.59 |
| | RH-92.5% | light yellow powder | 4.3 | 0.60 |
| | RH-75% | light yellow powder | 3.8 | 0.56 |
| | UV light | light yellow powder | 3.8 | 0.70 |

As seen from the data in Table 3, there was almost no change in appearance character and water content of Crystal form III of a compound of Formula (I) under various test conditions such as high temperature, high moisture, and light, i.e., Crystal form III had good stability; after Crystal form III was kept uncovered at high temperature of 60° C. for 5 days and 10 days, the total relevant substances increased by 0.28% and 0.44%, respectively, and there was little change; and under the condition of 60° C. covered and other test conditions, there was almost no change in total relevant substances, i.e., the samples had good stability.

Experimental Example 2. Evaluation on Pharmacokinetics of Crystal Form I, Crystal Form II, Crystal Form III and an Amorphous Compound in SD Rats Test sample: Crystal form I, Crystal form II and Crystal form III, the preparation methods of which could be found in the following Examples. An amorphous form of a compound of Formula (I), the preparation method of which could be found in the particular Examples as disclosed in the international patent application (Publication No. WO 2012027960 A1).

Test animal: SD rats, male, weighed 190-250 g, 6 rats for each crystal form, purchased from Beijing Vital River Laboratory Animal Technology Co., Ltd.

Experimental Method:

Drug preparation: for Crystal form I, the compound (15.00 mg) was weighed accurately, and sterilized water for injection (27.273 mL) was added; the compound was insoluble ultrasonically, and the mixture was mixed homogeneously under vortexing, to prepare a suspension (0.5 mg/mL); for Crystal form II, the compound (12.93 mg) was weighed accurately, and sterilized water for injection (24.168 mL) was added; the compound was insoluble ultrasonically, and the mixture was mixed homogeneously under vortexing, to prepare a suspension (0.5 mg/mL); for Crystal form III, the compound (13.34 mg) was weighed accurately, and sterilized water for injection (24.036 mL) was added; the compound was insoluble ultrasonically, and the mixture was mixed homogeneously under vortexing, to prepare a suspension (0.5 mg/mL); for the amorphous form, the compound (10.74 mg) was weighed accurately, and sterilized water for injection (21.244 mL) was added; the compound was insoluble ultrasonically, ground and wall sticking, heated, subjected to ultrasonic treatment, and mixed homogeneously under vortexing, to prepare a milk-white suspension.

Administration route: intragastric administration, at an administration dose of 5 mg/kg, and an administration volume of 10 mL/kg.

Blood collection: whole blood (about 100 μL) was collected from tail vein 10 min, 30 min, 1 h, 2 h, 4 h, 6 h, 8 h, and 24 h after administration, and added to $K_2$EDTA-containing anticoagulation tubes. The whole blood sample was centrifuged for 6 min at 4° C., 8000 rpm in a high speed centrifuge, and plasma was separated. Plasma needed to be prepared within 30 min after blood collection, and stored at −80° C. in a refrigerator.

Plasma sample analysis: the plasma samples were analyzed by protein precipitation: to plasma (20 μL), an internal standard Gefitinib (200 μL, 50 ng/mL acetonitrile solution) was added; the resultant mixture was vortexed at 500 rpm for 5 min, and centrifuged at 4000 rpm for 20 min in a high speed centrifuge; to the supernatant (100 μL), water (100 μL) was added; the resultant mixture was mixed homogeneously under vortexing and analyzed by LC-MS/MS for blood concentration.

Calculation for PK parameters: PK parameters were calculated by using Pharsight Phoenix 6.2 software.

Experimental Result:

TABLE 4

PK parameters of Crystal form I, Crystal form II, Crystal form III and an amorphous compound in SD rats

| Compound | $T_{1/2}$ (h) | $T_{max}$ (h) | $C_{max}$ (ng/mL) | $AUC_{0-t}$ (h*ng/mL) | $AUC_{inf}$ (h*ng/mL) |
|---|---|---|---|---|---|
| Crystal form I | 3.16 | 4 | 134 | 1404 | 1414 |
| Crystal form II | 4.59 | 3 | 135 | 1536 | 1591 |
| Crystal form III | 3.35 | 4 | 134 | 1324 | 1340 |
| Amorphous form | 3.08 | 4 | 105 | 1145 | 1152 |

$T_{1/2}$ represents drug elimination half-life, $T_{max}$ represents time to maximum blood concentration, $C_{max}$ represents maximum blood concentration, $AUC_{last}$ represents area under concentration-time curve from 0→t, $AUC_{inf}$ represents area under concentration-time curve from 0→∞

Experimental Conclusion:

As seen from the Experimental result in Table 4, the amorphous sample of a compound of Formula (I) had a significantly lower $C_{max}$ and exposure amount (AUC) than Crystal form I, Crystal form II and Crystal form III in SD rats, and the in vivo half-life of the amorphous form was also shorter than that of Crystal form I, Crystal form II and Crystal form III in SD rats, i.e., Crystal form I, Crystal form II and Crystal form III had good pharmacokinetic properties.

Experimental Example 3. Comparison of Stability Between Crystal Forms and an Amorphous Form of a Compound of Formula (I)

Test Conditions:

Crystal form I, Crystal form II, Crystal form III and an amorphous form of a compound of Formula (I) were kept uncovered at 60° C. for 10 days, and samples were taken at Day 5 and Day 10, respectively, and were observed for character and determined for relevant substances.

Test Sample:

Crystal form I, Crystal form II and Crystal form III of a compound of Formula (I), the preparation methods of which could be found in the following Examples; and an amorphous form of a compound of Formula (I), the preparation method of which could be found in the particular Examples as disclosed in the international patent application (Publication No. WO 2012027960 A1).

Methods for Determining Relevant Substances:

in accordance with High Performance Liquid Chromatography in General Rule 0512 of Pharmacopoeia of the People's Republic of China (2015), determination was performed by area normalization method.

Operation Condition

Instrument: High Performance Liquid Chromatographic Instrument (Agilent 1260 series)

Chromatographic column: chromatographic column using octylsilane chemically bonded silica as filler (HC-C$_8$, 4.6×250 mm, 5 µm)

Column temperature: 30° C.

Detection wavelength: 230 nm

Mobile phase: Mobile phase consisting of 0.06 mol/L sodium dihydrogen phosphate/0.06 mol/L sodium perchlorate solution-acetonitrile, and reversed-phase gradient elution was employed.

Flow rate: 1.0 mL/min

Injection volume: 10 µL

Experimental Result

TABLE 5

Result of stability of Crystal form I, II, III and an amorphous form of a compound of Formula (I)

| | Total relevant substances (%) | | | |
|---|---|---|---|---|
| Conditions | Amorphous form | Crystal form I | Crystal form II | Crystal form III |
| 0 day | 1.1 | 0.23 | 0.64 | 0.81 |
| 60° C. uncovered-5 days | 2.4 | 0.48 | 0.66 | 1.1 |
| 60° C. uncovered-10 days | 3.2 | 0.47 | 0.70 | 2.0 |

As seen from the data in Table 5, after being kept uncovered at 60° C. for 5 days and 10 days, Crystal form I, II and III had little increase in total relevant substances, i.e., had good stability; however, under the same test conditions, the amorphous form of a compound of Formula (I) had a rapid increase in total relevant substances, and as compared to the initial state at Day 0, the total relevant substances increased by 1.3% after being kept for 5 days, and increased by 2.1% after being kept for 10 days. Therefore, the stability of Crystal form I, II and III was significantly superior to that of the amorphous form at the condition of "60° C. uncovered".

EXAMPLES

The above contents of the invention are further illustrated in detail by reference to the following examples. However, the invention should not be limited to the following examples. Any technologies belong to the scope of the invention as long as they can be accomplished based on the contents of the invention. The experimental methods, for which no concrete conditions are indicated in the following examples, are selected according to conventional methods and conditions, or according to the instructions of products.

Example 1 Preparation I of Crystal Form I of a Compound of Formula (I)

A compound of Formula (I) (3 g, 5.9 mmol) was put in a round-bottom flask, and acetonitrile (45 mL) was added. The resultant mixture was heated to reflux. After the solution became clear, it was cooled naturally to room temperature, and solids were precipitated. After filtration, the solids were dried in vacuum, and dried at 50° C. in vacuum for 16 h, and the solids were identified as Crystal form I by XRPD test.

① X-ray powder diffraction (XRPD pattern, see FIG. 1):

Conditions for XRPD test (Cu-Kα radiation, 1.54 Å (monochromator), determined by D2 PHASER Type X-ray diffractometer), As determined by using Cu-Kα radiation, the XRPD pattern had characteristic peaks at the following 2θ positions: relatively strong characteristic peaks at the 2θ positions of 6.7, 7.9, 8.6, 12.0, 13.9, 15.9, 17.3, 18.3, 18.7, 21.0, and 23.0; characteristic peaks at the 2θ positions of 23.0, 23.4, 25.3, 26.0, 26.5, 27.7, and 28.0; and characteristic peaks at the 2θ positions of 13.6, 21.5, 21.9, and 32.2.

② DSC test (see FIG. 3):

Conditions for DSC test (Instrument Type: Q2000TA differential scanning calorimeter, under the protection of nitrogen, at a heating rate of 5° C./min)

The DSC thermogram had an endothermic conversion peak at 75-150° C., and a maximum endothermic conversion temperature of 113.85° C.

③ TGA test (determination of water of crystallization, see FIG. 2):

Conditions for TGA test (Instrument Type Q50TA, and heating to 350° C. at heating rate of 10° C./min)

The TGA thermogram showed that Crystal form I had a dehydration percent of 2.901% at 101.91° C., a dehydration percent of 0.312% at 149.2° C., and a total dehydration percent of 3.213%, which was close to the water content of 3.4% in theory.

Example 2 Preparation II of Crystal Form I of a Compound of Formula (I)

A compound of Formula (I) (3 g, 5.9 mmol) was put in a round-bottom flask, and acetonitrile (30 mL) was added. The resultant mixture was heated to reflux. After the solution became clear, water (1.5 mL) was added, and solids were precipitated immediately. The resultant mixture was cooled and then filtrated. The solids were identified as Crystal form I by XRPD test.

Example 3 Preparation III of Crystal Form I of a Compound of Formula (I)

A compound of Formula (I) (15 g, 29.4 mmol) was put in a round-bottom flask, and a mixed solvent of ethyl acetate and isopropanol (EA/IPA=10:1, 90 mL) was added. The resultant mixture was heated to reflux. After the solution became clear, it was cooled to 70° C. Water (18 mL) was added, and a lot of solids were precipitated under stirring. After further stirring at 60-65° C. for 3 h, it was cooled to 25° C. and stirred for 12 h. After filtration and drying at 50° C. in vacuum, solids (11.6 g, yield: 77%) were obtained, which were identified as Crystal form I by XRPD test.

Example 4 Preparation IV of Crystal Form I of a Compound of Formula (I)

A compound of Formula (I) (15 g, 29.4 mmol) was added to a reaction flask, and a mixture solvent of ethyl acetate and isopropanol (EA/IPA=10:1, 90 mL) was added. The resultant mixture was heated to reflux. After the solution became clear, water (0.75 mL, a sample amount of 5%) was added. After cooling to 60-70° C., n-heptane (90 mL) was added dropwise. The stirring was carried out at 40-45° C. for 4 h, and crystals were precipitated at 25° C. under stirring for 12 h. After suction filtration and drying at 50° C. in vacuum, solids (13.5 g, yield: 90%) were obtained, which were identified as Crystal form I by XRPD test.

Example 5 Preparation I of Crystal Form II of a Compound of Formula (I)

A compound of Formula (I) (3 g, 5.9 mmol) was put in a round-bottom flask, and ethyl acetate (35 mL) was added. The resultant mixture was heated to reflux. After the solution became clear, it was cooled to room temperature naturally, and solids were precipitated. After filtration and drying at 50° C. in vacuum for 16 h, the solids were obtained, which were identified as Crystal form II by XRPD test.

Ethyl formate, isopropyl acetate, or methyl acetate was used to replace the solvent ethyl acetate in Example 1, and Crystal form II could also be obtained by the same method.

① X-ray powder diffraction (XRPD pattern, see FIG. 4):
Conditions for XRPD test (Cu-Kα radiation, 1.54 Å (monochromator), determined by D2 PHASER Type X-ray diffractometer), As determined by using Cu-Kα radiation, the XRPD pattern had characteristic peaks at the following 2θ positions: relatively strong characteristic peaks at the 2θ positions of 6.9, 8.5, 14.8, 15.6, 16.7, 17.1, 17.9, 18.7, 19.1, 21.5, 23.5, and 25.7; characteristic peaks at the 2θ positions of 11.6, 17.3, 22.1, 26.1, and 28.3; and characteristic peaks at the 2θ positions of 14.0, 16.0, 19.7, 20.6, 22.4, 24.5, 28.6, 31.7, and 34.6, as determined by using Cu-Kα radiation.

② DSC test (see FIG. 5):
Conditions for DSC test (Instrument Type: Q2000TA differential scanning calorimeter, under the protection of nitrogen, at a heating rate of 5° C./min)

The DSC thermogram had an endothermic conversion peak at 75-169° C., and a maximum endothermic conversion temperature of 123.54° C.

③ TGA test (determination of water of crystallization, see FIG. 6):
Conditions for TGA test (Instrument Type: Q50TA, heating to 350° C. at heating rate of 10° C./min)

The TGA thermogram showed that Crystal form II had a dehydration percent of 2.389% at 121° C., a dehydration percent of 0.9164% at 170° C., and a total dehydration percent of 3.3%, which is close to the water content of 3.4% in theory.

Example 6 Preparation II of Crystal Form II of a Compound of Formula (I)

A compound of Formula (I) (3 g, 5.9 mmol) was put in a round-bottom flask, and a mixed solvent of ethyl acetate and methanol (EA/MeOH=20:1, 14 mL) was added. After heating to 70° C., water (0.15 mL, a sample amount of 5%) was added. When the solution was cooled to 40° C., it turned turbid, and solids were precipitated slowly. After further cooling to room temperature, the resultant mixture was filtrated and dried at 50° C. in vacuum for 16 h, to obtain solids (1.357 g, yield: 45.2%), which were identified as Crystal form II by XRPD test.

Example 7 Preparation III of Crystal Form II of a Compound of Formula (I)

A compound of Formula (I) (200 mg, 0.4 mmol) was put in a round-bottom flask, and toluene (30 mL) was added. After heating to 90° C., the solution became clear. After cooling, solids were precipitated, filtrated, and dried at 50° C. in vacuum. The solids were identified as Crystal form II by XRPD test.

Example 8 Preparation IV of Crystal Form II of a Compound of Formula (I)

To a compound of Formula (I) (4 g, 7.8 mmol), a mixed solvent of ethyl acetate and isopropanol (EA/IPA=15:1, 30 mL) was added. The resultant mixture was heated to reflux. After the solution became clear, water (0.2 mL, a sample amount of 5%) was added. After cooling to 45-50° C. slowly, crystals were precipitated for 4 h. After further cooling to 25° C. slowly under stirring for 12 h, the resultant mixture was subjected to suction filtration, and dried at 50° C. in vacuum, to obtain the product (2.8 g, yield: 70%), which was identified as Crystal form II by XRPD test.

Example 9 Preparation V of Crystal Form II of a Compound of Formula (I)

A compound of Formula (I) (5.8 g, 11.4 mmol) was put in a round-bottom flask, and a mixed solvent of isopropyl acetate (90 mL) and isopropanol (20 mL) was added. The resultant mixture was heated to reflux, and the solution became clear, and was cooled slowly to a temperature of 45-50° C. After precipitation of crystals for 4 h, the resultant mixture was further cooled to 25° C. slowly. After stirring for 12 h, the resultant mixture was subjected to suction filtration, and dried at 50° C. in vacuum, to obtain the product (2.7 g, yield: 46.6%), which was identified as Crystal form II by XRPD test.

Example 10 Preparation I of Crystal Form III of a Compound of Formula (I)

A compound of Formula (I) (3.0 g) was dissolved in isopropanol (30 mL) at 60° C. immediately, and the resultant solution was clear. Half an hour later, it was cooled to room temperature. After stirring for 2 h, solids were precipitated, and dried at 50° C. in vacuum for 16 h. The solids were identified as Crystal form III by XRPD test.

① X-ray powder diffraction (XRPD) of Crystal form III
Conditions for XRPD test: Cu-Kα radiation, 1.54 Å (monochromator), determined by D2 PHASER Type X-ray diffractometer.

XRPD: the XRPD pattern had relatively strong characteristic peaks at the 2θ positions of 4.9, 6.1, 7.4, 11.4, 12.2, 16.6, and 18.4; had characteristic peaks at the 2θ positions of 11.2, 13.4, 14.8, 19.2, 20.4, 20.8, 23.2, 23.8, 25.7, and 27.5; and had characteristic peaks at the 2θ positions of 9.2, 22.4, and 30.1. The result was shown in FIG. 7.

② DSC test of Crystal form III
Conditions for DSC test: Instrument Type: Q2000TA differential scanning calorimeter, under the protection of nitrogen, at a heating rate of 5° C./min.

The DSC thermogram analysis: it had an endothermic conversion peak at 50-125° C., and a maximum endothermic conversion temperature of 96.79° C. The result was shown in FIG. 9.

③ Determination of the water content of Crystal form III by TGA
Conditions for TGA test: Q50TA thermogravimetric analyzer, firstly, equilibrating at 40° C. for 10 min, followed by heating to 240° C. at heating rate of 10° C./min.

The water content determined by TGA: the TGA thermogram showed that Crystal form III had a dehydration percent of 2.686% at 50-100° C., which was close to the water content of 3.4% in theory, wherein the lost water was water of crystallization. The result was shown in FIG. 8.

Example 11 Preparation II of Crystal Form III of a Compound of Formula (I)

A compound of Formula (I) (2.0 g) was dissolved in acetone (50 mL) at room temperature, cyclohexane (400 mL) was added dropwise, and solids were precipitated. After stirring for 3 h, suction filtration was performed. The solids were dried at 45° C. in vacuum for 16 h, which were identified as Crystal form III by XRPD test.

Example 12 Preparation III of Crystal Form III of a Compound of Formula (I)

A compound of Formula (I) (3.0 g) was put in a round-bottom flask, and dichloromethane (30 mL) was added. The resultant mixture was heated to reflux. After the solution became clear, it was cooled naturally to room temperature. Solids were precipitated and filtrated. The solids obtained were dried at 50° C. in vacuum for 16 h, which were identified as Crystal form III by XRPD test.

The invention claimed is:

1. Crystal form I of N-(4-((3-chloro-4-fluorophenyl)amino)-7-((7-methyl-7-azaspiro[3.5]nonan-2-yl)methoxy)quinazolin-6-yl)acrylamide represented by Formula (I), wherein the Crystal form I exhibits an X-ray powder diffraction pattern having characteristic peaks at the 2θ positions of 6.7±0.2°, 7.9±0.2°, 8.6±0.2°, 12.0±0.2°, 13.9±0.2°, 15.9±0.2°, 17.3±0.2°, 18.3±0.2°, 18.7±0.2°, 21.0±0.2°, and 23.0±0.2°, as determined by using Cu-Kα radiation,

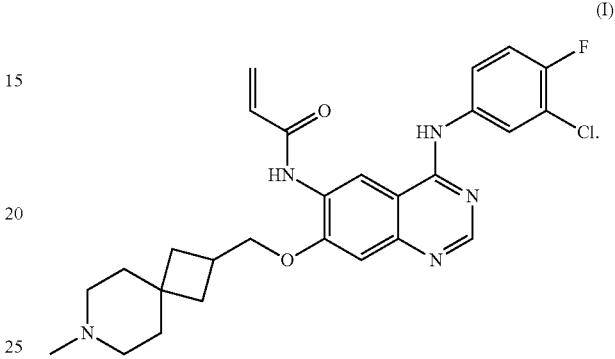

(I)

2. The Crystal form I according to claim 1, wherein the X-ray powder diffraction pattern further has characteristic peaks at the 2θ positions of 16.2±0.2°, 23.0±0.2°, 23.4±0.2°, 25.3±0.2°, 26.0±0.2°, 26.5±0.2°, 27.7±0.2°, and 28.0±0.2°, as determined by using Cu-Kα radiation.

3. The Crystal form I according to claim 2, wherein the X-ray powder diffraction pattern further has characteristic peaks at the 2θ positions of 13.6±0.2°, 21.5±0.2°, 21.9±0.2°, and 32.2±0.2°, as determined by using Cu-Kα radiation.

4. The Crystal form I according to claim 1, which exhibits a DSC thermogram having an endothermic conversion peak at 75-150° C., and a maximum endothermic conversion temperature of 113-114° C.

5. The Crystal form I according to claim 1, which is a hydrate having a water content of 2.5%-4%.

6. The Crystal form I according to claim 1, which is a monohydrate.

7. A method for preparing the Crystal form I according to claim 1, comprising the following steps: N-(4-((3-chloro-4-fluorophenyl)amino)-7-((7-methyl-7-azaspiro[3.5]nonan-2-yl)methoxy)quinazolin-6-yl)acrylamide is dissolved in a lower nitrile organic solvent or in a mixed solvent of a lower ester organic solvent and a lower alcohol organic solvent, and then subjected to addition of a poor solvent or recrystallization to produce a crystal, and then the crystal is subjected to filtration and drying to obtain Crystal form I.

8. The method according to claim 7, wherein the lower nitrile organic solvent is acetonitrile; the lower ester organic solvent is ethyl acetate or ethyl formate; the lower alcohol organic solvent is selected from the group consisting of methanol, ethanol and isopropanol; and the poor solvent is selected from water and/or n-heptane.

9. Crystal form II of quinazoline derivative N-(4-((3-chloro-4-fluorophenyl)amino)-7-((7-methyl-7-azaspiro[3.5]nonan-2-yl)methoxy)quinazolin-6-yl)acrylamide represented by Formula (I), wherein the Crystal form II exhibits a X-ray powder diffraction pattern having characteristic peaks at the 2θ positions of 6.9±0.2°, 8.5±0.2°, 11.6±0.2°, 14.0±0.2°, 14.8±0.2°, 15.6±0.2°, 16.0±0.2°, 16.7±0.2°, 17.1±0.2°, 17.3±0.2°, 17.9±0.2°, 18.7±0.2°, 19.1±0.2°, 19.7±0.2°, 20.6±0.2°, 21.5±0.2°, 22.1±0.2°, 22.4±0.2°, 23.5±0.2°, 24.5±0.2°, 25.7±0.2°, 26.1±0.2°, 28.3±0.2°, 28.6±0.2°, 31.7±0.2° and 34.6±0.2°, as determined by using Cu-Kα radiation,

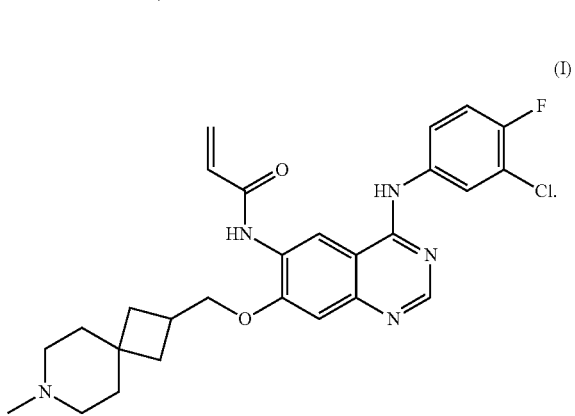

(I)

10. The Crystal form II according to claim 9, which exhibits a DSC thermogram having an endothermic conversion peak at 75-169° C., and a maximum endothermic conversion temperature of 123-124° C.

11. The Crystal form II according to claim 9, which is a hydrate having a water content of 3%-4%.

12. The Crystal form II according to claim 9, which is a monohydrate.

13. A method for preparing the Crystal form II according to claim 9, comprising the following steps: N-(4-((3-chloro-4-fluorophenyl)amino)-7-((7-methyl-7-azaspiro[3.5]nonan-2-yl)methoxy)quinazolin-6-yl)acrylamide is dissolved in a lower ester organic solvent, an aromatic hydrocarbon organic solvent, or a mixed solvent of a lower ester organic solvent and a lower alcohol organic solvent, and then subjected to addition of a poor solvent or recrystallization to produce a crystal, and then the crystal is subjected to filtration and drying to obtain Crystal form II;
wherein the lower ester organic solvent is selected from the group consisting of ethyl acetate, ethyl formate, methyl acetate and isopropyl acetate; the aromatic hydrocarbon organic solvent is toluene; the lower alcohol organic solvent is selected from the group consisting of methanol, ethanol and isopropanol; and the poor solvent is water.

14. Crystal form III of N-(4-((3-chloro-4-fluorophenyl)amino)-74(7-methyl-7-azaspiro[3.5]nonan-2-yl)methoxy)quinazolin-6-yl)acrylamide represented by Formula (I), wherein the Crystal form III exhibits an X-ray powder diffraction pattern having characteristic peaks at the 2θ positions of 4.9±0.2°, 6.1±0.2°, 7.4±0.2°, 9.2±0.2°, 11.2±0.2°, 11.4±0.2°, 12.2±0.2°, 13.4±0.2°, 14.8±0.2°, 16.6±0.2°, 18.4±0.2°, 19.2±0.2°, 20.4±0.2°, 20.8±0.2°, 22.4±0.2°, 23.2±0.2°, 23.8±0.2°, 25.7±0.2°, 27.5±0.2° and 30.1±0.2°, as determined by using Cu-Kα radiation,

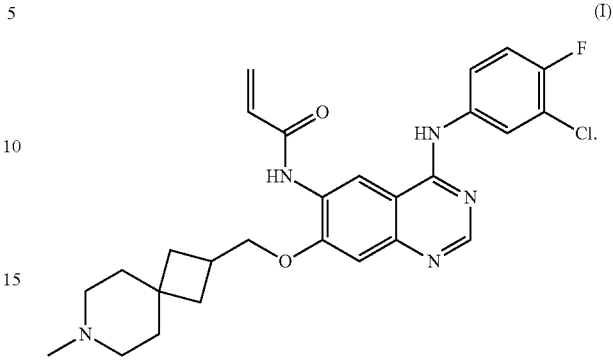

(I)

15. The Crystal form III according to claim 14, which exhibits a DSC thermogram having an endothermic conversion peak at 50-125° C., and a maximum endothermic conversion temperature of 96-97° C.

16. The Crystal form III according to claim 14, which is a hydrate having a water content of 2.5%-4%.

17. The Crystal form III according to claim 14, which is a monohydrate.

18. A method for preparing the Crystal form III according to claim 14, comprising the following steps: N-(4-(3-chloro-4-fluorophenyl)amino)-7-((7-methyl-7-azaspiro[3.5]nonan-2-yl)methoxy)quinazolin-6-yl)acrylamide is subjected to recrystallization using a lower alcohol organic solvent or a lower halo hydrocarbon organic solvent to produce a solid, and then the solid is subjected to filtration and drying to obtain Crystal form III;
wherein the lower alcohol organic solvent is selected from the group consisting of methanol, ethanol and isopropanol; and the lower halo hydrocarbon organic solvent is dichloromethane.

19. A method for preparing the Crystal form III according to claim 14, comprising the following steps: N-(4-((3-chloro-4-fluorophenyl)amino)-7-((7-methyl-7-azaspiro[3.5]nonan-2-yl)methoxy)quinazolin-6-yl)acrylamide is dissolved in a lower ketone organic solvent, and then subjected to addition of an alicyclic hydrocarbon organic solvent dropwise to produce a solid, and then the solid is subjected to filtration and drying to obtain Crystal form III;
wherein the lower ketone organic solvent is selected from the group consisting of acetone and butanone; and the alicyclic hydrocarbon organic solvent is selected from the group consisting of cyclopentane and cyclohexane.

20. A pharmaceutical formulation, comprising the Crystal form I according to claim 1, and one or more pharmaceutically acceptable carriers and/or diluents.

* * * * *